United States Patent [19]
Gray et al.

[11] Patent Number: 5,723,446
[45] Date of Patent: *Mar. 3, 1998

[54] ENTERAL FORMULATION DESIGNED FOR OPTIMIZED NUTRIENT ABSORPTION AND WOUND HEALING

[75] Inventors: Debora Gray, Evanston; Nancy S. Schmelkin, Buffalo Grove; John Alexander, Kenilworth; David A. Mark, Oak Park; Diana Twyman, Chicago, all of Ill.

[73] Assignee: Nestec Ltd., Vevey, Switzerland

[*] Notice: The term of this patent shall not extend beyond the expiration date of Pat. No. 5,714,472.

[21] Appl. No.: 680,703

[22] Filed: Jul. 17, 1996

Related U.S. Application Data

[63] Continuation of Ser. No. 172,857, Dec. 23, 1993, abandoned.

[51] Int. Cl.⁶ .............................. A61K 38/00; A23J 1/00; A23G 3/00
[52] U.S. Cl. ...................... 514/21; 514/2; 514/23; 514/54; 514/538; 514/560; 514/94.3; 426/72; 426/607; 426/656; 426/658; 424/DIG. 13
[58] Field of Search ................ 514/21.2, 23.54, 514/558, 560, 943; 426/72, 607, 656, 658; 424/DIG. 13

[56] References Cited

U.S. PATENT DOCUMENTS

| | | | |
|---|---|---|---|
| 4,670,268 | 6/1987 | Mahmoud | 426/72 |
| 4,753,963 | 6/1988 | Jaudacek et al. | 514/552 |
| 4,920,098 | 4/1990 | Cotter et al. | 514/2 |
| 4,931,300 | 6/1990 | Monte | 426/335 |
| 5,053,387 | 10/1991 | Alexander | 514/2 |
| 5,055,446 | 10/1991 | Alexander et al. | 514/2 |
| 5,156,875 | 10/1992 | Monte | 426/532 |
| 5,166,189 | 11/1992 | Trunbo et al. | 514/2 |
| 5,221,668 | 6/1993 | Henningfield et al. | 514/23 |
| 5,223,285 | 6/1993 | De Michele et al. | 426/72 |
| 5,260,279 | 11/1993 | Greenberg | 514/21 |
| 5,438,042 | 8/1995 | Schmidl et al. | 514/21 |

FOREIGN PATENT DOCUMENTS 0189160  7/1986  European Pat. Off. .

OTHER PUBLICATIONS

Ross Laboratories Brochure, *Specialized Elemental Nutrition With Glutamine—The Role of ALITRAQ™ Specialized Elemental Nutrition With Glutamine* (1991).
Ross Laboratories Brochure, *Introducing ALITRAQ™ Specialized Elemental Nutrition With Glutamine* (1992).
Ross Laboratories Brochure, *Introducing PERATIVE™* (1992).
Sandoz Nutrition Brochure, *IMPACT®* (1993).
Sandoz Nutrition Brochure, *INTRODUCING IMPACT®* (1989).
Sandoz Nutrition Brochure, *IMPACT®* (1991).
Mead Johnson, *Enteral Nutritionals Product Handbook*, bearing Nos. A2688–2693.
Mead Johnson Enteral Nutritionals Brochure bearing No. B00083.
Mead Johnson Brochure bearing Nos. B00322–B00323.
Mead Johnson, *Metabolic and Nutrition Support for Trauma and Burn Patients A Symposium*, Abstracts, pp. 1–13 (1982).
*Nutritional Care of Metabolically Stressed Patients*, Proceedings from the Metabolic and Nutrition Support for Trauma and Burn Patients Symposium, White Sulphur Springs, West Virginia, pp. 1–77 (1983).
*Principles of Nutritional Support: Proceedings From the Metabolic and Nutrition Support for Trauma and Burn Patients Symposium*, White Sulphur Springs, West Virginia, pp. 1–25 (1982).
*Symposium Highlights Metabolic and Nutrition Support for Trauma and Burn Patients*, White Sulphur Springs, West Virginia, pp. 1–26 (1982).
*TraumaCal, Feeding the Hypermetabolic Patient, Clinical Experience*, A Symposium, pp. 1–74 (1983).
TraumaCal Product Cards bearing Nos. B000001–B000010.
TraumaCal Documents bearing Nos. B00088–B00105.
TraumaCal Document bearing No. B00181.
TraumaCal Document bearing Nos. B00261–B00265.
TraumaCal Document bearing No. B00293.
TraumaCal Document bearing Nos. B00384–B00385.
TraumaCal Label bearing No. B00441.
TraumaCal Brochure bearing Nos. B00567–B00570.
Cerra et al, *Surgery*, vol. 98, No. 4, pp. 632–639, Oct. 1985.
Wilmore et al, *Surgery*, vol. 104, No. 5, pp. 917–923, Nov. 1988.
Alexander, Abstract (Medline—Search Report) (Arch. Surg., vol. 128, No. 11, pp. 1242–1245, Nov. 1993).

*Primary Examiner*—Cecilia J. Tsang
*Assistant Examiner*—Abdel A. Mohamed
*Attorney, Agent, or Firm*—Hill, Steadman & Simpson

[57] ABSTRACT

The present invention provides an enteral nutritional formulation that meets the nutrient requirements of intensive care patients who may have compromised absorption capacity. The present invention meets the unique nutrient needs of the patient that are generated due to tissue repair and healing requirements. To this end, in an embodiment the present invention provides a method for treating and/or providing nutritional support to intensive care patients comprising the steps of administering a therapeutically effective amount of a composition comprising: a protein source; a carbohydrate source; and a lipid source including a source of medium chain triglycerides, a source of omega-3 fatty acids, and a source of omega-6 fatty acids.

26 Claims, No Drawings

ENTERAL FORMULATION DESIGNED FOR OPTIMIZED NUTRIENT ABSORPTION AND WOUND HEALING

This is a continuation of application Ser. No. 08/172,857, filed Dec. 23, 1993 now abandoned.

BACKGROUND OF THE INVENTION

The present invention relates to nutritionally fortified pharmaceutical compositions. More specifically, the present invention relates to compositions for use in intensive care patients.

Intensive care patients describe a broad population of patients who may suffer from a variety of diseases or insults. These patients, however, exhibit some similar requirements. For example, patients suffering from traumatic injury, burns, post-surgery, and some disease states have a significant need for increased nutrients and energy as compared to individuals who are not challenged by such metabolic stress.

Indeed, non-essential nutrients and substances that a body typically can synthesize in adequate supply, may become limiting. Additionally, absorption of nutrients from the gut can be compromised even when there is no direct injury to the gastrointestinal system.

Many intensive care patients are fed either with parenteral formulations or enteral formulations either to replace or supplement a typical diet. For example, in 1991, of an estimated 2.4 million trauma patients in the United States, 13% (310,000) required nutrition support beyond food. Of these patients, 62% of the patients were supported using enteral nutrition, 70% tube-feeding, and 30% oral supplements, while 38% were initially supported using parenteral nutrition and progressed to tube-feeding, if they survived. Similarly, of about 106,000 burn patient admissions in 1991 in the U.S., approximately 20% (21,000) required nutritional support. Of this group, 95% were started on enteral nutrition, 70% began on tube feeding and 30% started on oral supplements.

Numerous enteral formulations have been targeted for trauma and burn patients. These products include: Mead-Johnson's TRAUMACAL®; Sandoz's IMPACT®; Abbott Laboratories' ALITRAQ®; and McGaw's IMMUN-AID®.

Although such products are used in an attempt to treat and/or provide nutritional requirements for such patients, the inventors of the present invention do not believe that these products meet the needs of such patients.

Accordingly, there is a need for an enteral nutritional formulation which meets the nutrient requirements of intensive care patients who may have altered nutritional requirements and compromised absorptive capacity.

SUMMARY OF THE INVENTION

The present invention provides an enteral nutritional formulation that meets the nutrient requirements of intensive care patients who may have compromised absorption capacity. The present invention meets the unique nutrient needs of the patient that are generated due to tissue repair and healing requirements.

To this end, in an embodiment the present invention provides a method for treating and/or providing nutritional support to intensive care patients comprising the steps of administering a therapeutically effective amount of a composition comprising: a protein source; a carbohydrate source; and a lipid source including a source of medium chain triglycerides (MCTs), a source of omega-3 fatty acids, and a source of omega-6 fatty acids. In an embodiment, the source of omega-3 fatty acids comprises at least 2.3% of the total calories.

In an embodiment, a method for treating and/or providing nutritional support to an intensive care patient is provided comprising administering a therapeutically effective amount of a composition comprising: a high protein content of at least 22% of the total calories; a carbohydrate source; and a high lipid content of at least 30% of the total calories.

In an embodiment, a method for treating an intensive care patient is provided comprising administering a therapeutically effective amount of a composition comprising: 22-28% of the calories as a protein; 33-45% of the calories as a lipid, the lipid provides at least 40% of its caloric content as medium chain triglycerides, and further including an omega-3 fatty acid source and an omega-6 fatty acid source; and a carbohydrate source. Preferably, the caloric density of the composition is at least 1.3 Kcal/ml.

If desired the composition can include sources of: glutamine; arginine; proline; and/or cysteine.

It is an advantage of the present invention that it provides an enteral nutritional formulation that is designed to optimize nutrient absorption and wound healing in trauma patients.

Moreover, an advantage of the present invention is to provide a composition having a high protein content, a high lipid content, and a high caloric density to meet protein and energy needs.

Furthermore, an advantage of the present invention is to provide a composition that has reduced water and carbohydrate content reducing the risk of diarrhea due to carbohydrate intolerance, hyperglycemia, over hydration, and the like.

Still further, an advantage of the present invention is that nutrient malabsorption is reduced by the absence of whole proteins and by the use of protein hydrolysate, free amino acids and medium chain triglycerides in the enteral formulation of the present invention.

Additionally, an advantage of the present invention is that it is a ready-to-use formulation, and not a powder that requires mixing before use, reducing the risk of bacterial contamination during the mixing process.

Moreover, pursuant to the present invention, healing and tissue repair/cell division is promoted by the use of certain components.

It is also an advantage of the present invention that inflammatory reactions are minimized.

Additional features and advantages of the present invention are described in, and will be apparent from, the detailed description of the presently preferred embodiments.

DETAILED DESCRIPTION OF THE PRESENTLY PREFERRED EMBODIMENTS

The present invention provides enteral formulations specifically designed for use with intensive care patients, specifically, trauma, burn, and post-surgery patients. Moreover, the present invention provides methods of treating such patients.

Pursuant to the present invention, an enteral formulation is provided that is designed to optimize nutrient absorption and wound healing in trauma patients. The enteral formulation of the present invention meets the nutrient requirements of such patients with compromised absorptive capacity. The formulation also meets nutrient needs unique to tissue repair and healing of the patients.

Generally, pursuant to the present invention, a ready-to-use enteral formulation is provided. The formulation can provide the total nutritional requirements of the intensive care patient or can act as a supplement. The product is designed preferably to be fed to the patient by tube. The product can be provided, for example, in cans or a spike and hang bag. The product is ready to use and does not require reconstitution or mixing prior to use.

In a preferred embodiment, the enteral formulation has a high caloric content. In an embodiment, preferably, the caloric content is between approximately 1.3 to about 1.5 Kcal/ml. It is necessary to provide a moderate-to-high caloric intake to spare protein. Caloric needs in severe trauma, burn, and post-surgical patients typically range from 25 to about 35 Kcal/Kg, e.g., 1800 to 2300 Kcal for a convalescing 70 Kg adult. In fact, severe burn patients can require even higher caloric needs.

Additionally, due to increased metabolic activity, such patients require high protein intake to reduce negative nitrogen balance and support wound repair. Protein needs average 2.0 g of protein Kg body weight or, e.g., 140 grams of protein per day for a convalescing 70 Kg adult. Therefore, the formulation has a high protein content, preferably at least approximately 22% of the calories of the product are provided as protein. In an embodiment, up to 28% of the calories are provided as protein.

A variety of proteins can be utilized. In an embodiment, the protein is hydrolyzed casein plus free amino acids. If desired, the protein source can be high in glutamine and perhaps in cysteine. In an embodiment, the protein source is enriched with arginine and proline as free amino acids.

The use of protein hydrolysate and free amino acids reduces the potential for nutrient malabsorption. Additionally, by providing a high glutamine, arginine, protein and/or cysteine content, wound healing and tissue repair/cell division is promoted.

In an embodiment, 25% of the total caloric content of the product is protein. In an embodiment, 80–85% of the protein will be partially hydrolyzed casein, 13–15% arginine and 4–6% proline. In an embodiment, 68–70% of the protein will be partially hydrolyzed casein, 17–20% will be partially hydrolyzed whey protein and 13–15% will be arginine. In a preferred embodiment, 85–88% of the protein will be partially hydrolyzed casein and 12–15% will be arginine. In choosing the protein source, the present invention maximizes the naturally available levels of desirable amino acids such as arginine, cysteine, proline and glutamine at the highest bioavailability and product stability.

The formulation of the present invention includes a lipid fraction. Preferably, approximately 33% to about 45% of the formulation, by calories, is provided as a lipid. In a preferred embodiment, 39% of the calories are provided as a lipid.

The lipid fraction contains significant amounts of omega-3 rich fatty acids and medium chain triglycerides. Preferably, the lipid fraction comprises approximately 40% to about 60%, by calories MCTs. MCTs are more easily absorbed and metabolized as compared to long chain triglycerides (LCTs). The use of MCT will reduce the risk of the potential for nutrient malabsorption. A low omega-6 content and a high omega-3 content are provided. Preferably, the ratio of omega-6 to omega-3 fatty acids is less than 2.0:1. The low omega-6: omega-3 ratio reduces the incidence and severity of inflammatory reactions. Omega-3 fatty acids may modulate the negative, immune-mediated reactions brought about by high omega-6 intake. Therefore, oil blends which contain omega-3 (or are, at a minimum, low in omega-6) are preferred.

Accordingly, in an embodiment, a fish oil rich in omega-3 fatty acids is preferred, as fish oils contain two longer chain length omega-3 fatty acids: eicosapentaenoic acid (EPA, C22:5, n3) and docosahexaenoic acid (DHA, C22:6, n3). Soy oil is also preferred, in that it contains approximately 7% linolenic acid (C18:3, n3), in order to insure that a safe minimum level of shorter length omega-3 fatty acids is delivered, and also contains approximately 50–55% linoleic acid (C18:2, n-6), in order to insure that a safe minimum level of omega-6 fatty acids is delivered (essential fatty acids). In an embodiment of the present invention, the lipid component comprises by weight 50% MCT, 25% fish oil and 25% soy oil (includes soy oil and soy lecithin).

In addition to the ability of omega-3 to modulate inflammatory reactions, likewise, the antioxidant vitamins and minerals also reduce the incidence of severity of inflammatory reactions.

By utilizing a formulation having high protein and fat content, protein and energy requirements are met. However, at the same time, pursuant to the present invention, the formulation includes reduced water and carbohydrate content. This reduces the risk of over hydration, hyperglycemia, and carbohydrate intolerance.

Preferably, the formulation is approximately 35% to about 40%, by calories, carbohydrates. By way of example, the carbohydrates can be chosen from maltodextrin, corn starch, sucrose, and corn syrup solids.

In an embodiment, the present invention includes soluble or insoluble fiber, and/or carob pod powder or extract that is rich in insoluble tannins. In an enteral product, especially one to be provided by tube feeding, this provides anti-diarrhea characteristics. Magnesium can be reduced below U.S. RDA levels (400 mg/day), further limiting the potential for tube-fed induced diarrhea. An example of the use of tannins to reduce the incidence of diarrhea is set forth in U.S. patent application Ser. No. 887,360 entitled: "ENTERAL FORMULATION DESIGNED TO REDUCE DIARRHEA IN TUBE-FED PATIENTS" now abandoned, the disclosure of which is hereby incorporated herein by reference.

Preferably, anti-oxidant vitamins and minerals are increased to above the U.S. RDAs. This will insure that the patient receives at least 100% of the U.S. RDA as well as insure that any additional micronutrients that are necessary due to the patient's state will be provided. The formulation, in an embodiment, will provide approximately 5–6 mg/1500 Kcal of beta-carotene. Beta-carotene is a precursor for Vitamin A and has some unique antioxidant properties.

Of course, it will be appreciated that a variety of formulations are possible in accordance with the present invention. An example of a formulation in accordance with the present invention includes a formulation having a caloric density of 1.5 Kcal/ml. This is equivalent to 375 Kcal/250 ml which will, in a preferred embodiment, by one unit (can or container) of product.

In this embodiment, preferably, protein comprises 25%, by calories, of the product. This is equivalent to 94 grams/liter. A variety of different components are possible for the protein portion of the product. In an embodiment, casein plus arginine can be utilized. In a further embodiment, casein plus arginine plus proline can be utilized for the protein component.

Preferably, in this embodiment, the lipid component comprises approximately 39% of the calories of the product. This will be equal to approximately 65 grams/liter. In the embodiment, approximately 50% of the lipid component is MCTs and 25% of the lipid component is fish oil. Preferably, 19 to 21% of the lipid component is soy oil and 4–6% soy lecithin. This will provide an omega-6:omega-3 ratio of approximately 1.8:1.

Preferably, in this embodiment, the carbohydrates comprise 36% of the calories. This is equivalent to 135 g/l. In the embodiment, maltodextrin and corn starch are used.

The total calories/nitrogen in this embodiment is approximately 90:1. The total non-protein calories/grams of nitrogen is approximately 67:1. Osmolality will be less than or equal to 500 mOsm/kg $H_2O$. It is envisioned that the shelf-life of the product will be approximately 12 months.

Pursuant to the present invention, the omega-3 fatty acids as a percent of the total calories of the product will be greater than 2.3%. Anti-inflammatory activity is believed to be achieved at 2.2% to 3% of the calories of the product. Anti-thrombotic and hypolipidemic is also believed to be a benefit of such high levels of omega-3. As set forth above, preferably, fish oil and soy oil are utilized. A number of potential beneficial effects are achieved by using fish oil.

Most typical nutritional products have less than 2.3% of the total calories as omega-3 fatty acids. To this end, the following commercial available products have the following omega-3 fatty acid content (as a % of total calories): IMPACT® 1.6%; IMMUN-AID® 1.0%; PEPTAMEN® VHP 1%; Promote 0.9%; TRAUMACAL® 0.3%; and PEPTAMEN® 0.2%.

In an embodiment of the present invention, the formulation of the present invention includes at least 3% of the total calories as arginine. Enhanced wound healing with arginine is believed to be provided at quantities greater than 3% of the total calories.

Additionally, in an embodiment, the present invention includes significant amounts of proline. In an embodiment, the proline content is at least 2.0% of the total calories. Proline content as a percent of specific proteins is as follows: gelatin=16.1%; casein=9.6%; whey=5.7%; and soy=5.4%.

Additionally, in an embodiment, the present invention can include significant amounts of cysteine. In an embodiment, the present invention only provides approximately 0.6% of the total calories as cysteine. This is substantially in line with ad-libitum diets. However, the present invention, in an embodiment, provides 0.17% of the total calories as cysteine. Cysteine content of various proteins is as follows: casein=0.3%; total milk products=0.9%; soy protein=1.2%; whey protein=2.0%; and egg white protein=2.5%.

Pursuant to the present invention, non-protein calories/ grams of nitrogen (NPC/gN) is determined so as to provide a composition that spares the use of proteins as the calorie source. Patients with severe metabolic stress (trauma, burns) preferably should receive a product with an NPC/gN of less than 100:1 because of their increased protein requirements. Pursuant to the present invention, the formulation provides compositions having less than or equal to 70:1. The weight/ nitrogen weight of certain proteins is as follows: arginine 3.11:1; glutamine 5.21:1; casein 6.25:1; protein 6.25:1; whey 6.38:1; proline 8.21:1; branched chain amino acids 8.79:1.

By way of example, and not limitation, examples of formulations of the present invention will now be given.

FORMULA EXAMPLE NO. 1

A liquid, ready-to-use enteral product with protein at 25% of total calories: 87% from partially hydrolyzed casein and 13% from the free amino acid arginine. Carbohydrates would be 35–40% of calories. Lipids comprise 38–42% of calories, preferably a blend of medium chain triglycerides (50%), fish oil (25%), soy oil and soy lecithin (25% total of both soys). Vitamin and mineral content would meet preferably daily requirements in 1500 calories.

FORMULA EXAMPLE NO. 2

A liquid, ready-to-use enteral product with protein at 25% of total calories: 60% from partially hydrolyzed casein, 20% from partially hydrolyzed whey protein, 15% from the free amino acid arginine and 5% from the free amino acid proline. Carbohydrates would be 35–40% of calories. Lipids comprise 38–42% of calories, preferably a blend of medium chain triglycerides (50%), fish oil (25%), soy oil and soy lecithin (25% total of both soys). Vitamin and mineral content would meet preferably daily requirements in 1500 calories.

By way of example, and not limitation, contemplative examples of the use of the present invention will now be given.

CONTEMPLATIVE EXAMPLE NO. 1

Two hundred patients admitted to intensive care units with moderate to severe trauma are nutritionally supported by the use of tube-fed enteral formulas. Half receive a whole protein based product at 1.0 calories/mL, with protein as 22% of calories (a combination of whole protein and free amino acid arginine), carbohydrates at 50–55% of calories and lipids at 20–25% of calories, with 25% as MCT and the remainder fish oil and sunflower oil. Vitamin and mineral U.S. RDAs met in 1500 calories (1500 mL). Half receive a formula described in this invention: a liquid, ready-to-use enteral product at 1.3–1.5 Kcal/mL with protein at 25% of total calories (87% from partially hydrolyzed casein and 13% from the free amino acid arginine), carbohydrates at 35–40% calories and lipids at 38–42% of calories, with half of the lipid as MCT, 25% fish oil and 25% soy oil and soy lecithin. Vitamin and mineral U.S. RDAs met in 1500 calories (1000 mL).

Many of the patients receiving the whole protein diet were unable to receive the recommended calorie and protein intakes of 2200–2500 calories and 140 grams protein because of intolerance and diarrhea and conflicts with the need to not overhydrate. By comparison, the elemental and calorically dense product described in this invention, it is believed, will be able to deliver 2250 calories and 140 grams protein in 1.5 liters/day with a minimal incidence of intolerance or diarrhea. When using APACHE scoring to predict outcomes, the patients fed the enteral diet described in this invention will, it is believed, have a shorter average length of stay and fewer inflammatory complications than would have been expected based on experiences with whole protein-based diets which contain less than 2.3% of calories as a mixture of omega-3 fatty acids (linolenic, EPA and DHA).

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A method for providing nutrition to a trauma, burn or post-surgery patient comprising the step of enterally administering to the patient a therapeutically effective amount of a composition comprising:

a protein source comprising at least 25% of the total calories;

a carbohydrate source comprising approximately 35% to about 40% of the total calories; and a lipid source comprising approximately 33% to about 45% of the total calories including a source of medium chain triglycerides comprising approximately 40% to about 60% of the lipid source, a source of omega-3 fatty acids, and a source of omega-6 fatty acids.

2. The method of claim 1 wherein the omega-3 source provides approximately 2.2% to about 3% of the total calories.

3. The method of claim 1 wherein the composition provides a source of arginine.

4. The method of claim 1 wherein the composition provides a source of proline.

5. The method of claim 1 wherein the protein source includes a majority of the protein calories as partially hydrolyzed proteins and does not contain whole proteins.

6. The method of claim 1 wherein the formulation is fed through a tube to the patient.

7. The method of claim 1 wherein the composition includes a source of beta-carotene.

8. A method for providing nutrition to a trauma, burn or post-surgery patient comprising the step of enterally administering to the patient a therapeutically effective amount of a composition comprising:

a high protein source comprising approximately 22% to about 28% of the total calories, the protein source includes a majority of the protein calories as partially hydrolyzed proteins and does not contain whole proteins;

a carbohydrate source of approximately 35% to about 40% of the total calories; and a lipid source of approximately 33% to about 45% of the total calories, the lipid source comprising at least 40%, by calories, medium chain triglycerides.

9. The method of claim 8 wherein approximately 2.2% to about 3% of the total calories are provided by omega-3 fatty acids.

10. The method of claim 8 wherein the composition provides a source of arginine.

11. The method of claim 8 wherein the composition provides a source of proline.

12. The method of claim 8 wherein the composition includes a source of beta-carotene.

13. A method for providing nutrition to a trauma, burn or post-surgery patient comprising the step of enterally administering a therapeutically effective amount of a composition comprising:

approximately 22% to about 28% of the total calories as protein;

approximately 33% to about 45% of the total calories as a lipid including a source of medium chain triglycerides and an omega-3 fatty acid source providing at least 2.3% of the total calories;

approximately 35% to about 40% of the total calories as a carbohydrate source; and the composition having a caloric density of approximately 1.3 to about 1.5 Kcal/ml.

14. The method of claim 13 wherein the composition provides a source of arginine.

15. The method of claim 13 wherein the composition provides a source of proline.

16. The method of claim 13 wherein the protein source includes a majority of the total calories as partially hydrolyzed proteins.

17. The method of claim 13 wherein the lipid source includes approximately 40% to about 60% of the lipid calories as medium chain triglycerides.

18. The method of claim 13 wherein the composition includes a source of beta-carotene.

19. A composition for providing nutrition to a trauma, burn or post-surgery patient comprising:

approximately 22–28% of the calories as a protein source, the protein source including approximately 68% to about 88% partially hydrolyzed protein;

approximately 35–45% of the calories as a lipid including approximately 40% to about 60% as medium chain triglycerides, an omega-3 fatty acid source, and an omega-6 fatty acid source;

approximately 35% to about 40% of the calories as a carbohydrate source; and the caloric density of the composition being approximately 1.3 to about 1.5 Kcal/ml.

20. The composition of claim 19 wherein the composition includes a source of arginine.

21. The composition of claim 19 wherein the composition includes a source of proline.

22. The composition of claim 19 wherein the composition includes a source of cysteine.

23. The composition of claim 19 wherein the composition includes a source of beta-carotene.

24. The composition of claim 19 wherein the protein source includes approximately 80% to about 85% partially hydrolyzed protein.

25. A composition for providing nutrition to a trauma, burn or post-surgery patient comprising:

approximately 22–28% of the calories as a protein;

approximately 35–45% of the calories as a lipid including approximately 40% to about 60% as medium chain triglycerides, an omega-3 fatty acid source, and an omega-6 fatty acid source;

approximately 35%–40% of the calories as a carbohydrate source; and approximately 12% to about 15% of the protein calories being provided by arginine.

26. A composition for providing nutrition to a trauma, burn or post-surgery patient comprising:

approximately 22–28% of the calories as a protein;

approximately 35–45% of the calories as a lipid including approximately 40% to about 60% as medium chain triglycerides, an omega-3 fatty acid source and an omega-6 fatty acid source;

approximately 35%–40% of the calories as a carbohydrate source; and approximately 4% to about 6%, by protein calories, of the composition being provided by proline.

* * * * *